(12) United States Patent
Yamamoto et al.

(10) Patent No.: US 9,335,324 B2
(45) Date of Patent: May 10, 2016

(54) ASSAY METHOD AND KIT FOR ASSAY EMPLOYING SENSOR CHIP FOR FLUORESCENT MEASURING APPARATUS UTILIZING SURFACE PLASMON-FIELD ENHANCED FLUORESCENCE SPECTROMETRY

(75) Inventors: Noriaki Yamamoto, Foster City, CA (US); Takatoshi Kaya, Inagi (JP)

(73) Assignee: KONICA MINOLTA, INC. (JP)

(*) Notice: Subject to any disclaimer, the term of this patent is extended or adjusted under 35 U.S.C. 154(b) by 1135 days.

(21) Appl. No.: 13/353,508

(22) Filed: Jan. 19, 2012

(65) Prior Publication Data
US 2012/0196385 A1 Aug. 2, 2012

(30) Foreign Application Priority Data

Jan. 27, 2011 (JP) ................................. 2011-014877

(51) Int. Cl.
*G01N 33/553* (2006.01)
*G01N 21/64* (2006.01)
*G01N 33/543* (2006.01)

(52) U.S. Cl.
CPC ............ *G01N 33/553* (2013.01); *G01N 21/648* (2013.01); *G01N 21/6428* (2013.01); *G01N 33/54373* (2013.01); *G01N 2610/00* (2013.01)

(58) Field of Classification Search
None
See application file for complete search history.

(56) References Cited

U.S. PATENT DOCUMENTS

| 5,436,161 | A  | * | 7/1995  | Bergstrom et al. | ............ 422/425 |
| 7,229,840 | B1 |   | 6/2007  | Wischerhoff      |                     |
| 7,563,623 | B2 | * | 7/2009  | Ezoe et al.      | ..................... 436/524 |
| 8,183,057 | B2 |   | 5/2012  | Isojima et al.   |                     |
| 2007/0258866 | A1 | * | 11/2007 | Nishimi et al. | ................ 422/129 |
| 2009/0275721 | A1 | * | 11/2009 | Cooper et al.  | ................. 527/207 |

FOREIGN PATENT DOCUMENTS

| JP | 3294605 B2 | 4/2002 |
| JP | 2006113050 A | 4/2006 |
| JP | 2007256268 A | 10/2007 |
| JP | 2010-145202 A | 7/2010 |
| WO | 2010123073 A1 | 10/2010 |
| WO | 2010134592 A1 | 11/2010 |

OTHER PUBLICATIONS

Extended European Search Report for Application No./Pat. No. 12151689.2-2204, dated May 9, 2012.
Green R.J. et al., "Surface plasmon resonance analysis of dynamic biological interactions with biomaterials", Biomaterials, Elsevier Science Publishers BV., Barking, GB, vol. 21, No. 19, Sep. 1, 2000, pp. 1823-1835.

(Continued)

*Primary Examiner* — Chris L Chin
(74) *Attorney, Agent, or Firm* — Cantor Colburn LLP

(57) ABSTRACT

An assay method with use of a sensor chip which includes a metal member, a self-assembled monolayer (SAM), and ligands on a support, and is configured to be used for a fluorescence measuring apparatus with utilization of a surface plasmon-field enhanced Fluorescence Spectrometry, including the steps of: forming a hydrophilic high molecule layer on the self-assembled monolayer in the sensor chip; immobilizing the ligands at least one of in the hydrophilic high molecule layer and on the surface of the hydrophilic high molecule layer; and bringing a moisturizer in contact with the hydrophilic high molecule layer.

18 Claims, 2 Drawing Sheets

(56) References Cited

OTHER PUBLICATIONS

O'Shannessy D.J. et al., "Immobilization chemistries suitable for use in the BIAcore surface plasmon resonance detector", Analytical Biochemistry, Academic Press Inc, New York, vol. 205, No. 1, Aug. 15, 1992, pp. 132-136.

Japanese Notification of Reason for Rejection corresponding to Patent Application No. 2012-005076; Date of Mailing: Dec. 16, 2014, with English translation.

Green R.J. et al., "Surface plasmon resonance analysis of dynamic biological interactions with biomaterials", Biomaterials, Elsevier Science Publishers BV., Barking, GB, vol. 21, No. 18, Sep. 1, 2000, pp. 1823-1835.

* cited by examiner

ASSAY METHOD AND KIT FOR ASSAY EMPLOYING SENSOR CHIP FOR FLUORESCENT MEASURING APPARATUS UTILIZING SURFACE PLASMON-FIELD ENHANCED FLUORESCENCE SPECTROMETRY

This application is based on Japanese Patent Application No. 2011-014877 filed on Jan. 27, 2011, in Japanese Patent Office, the entire content of which is hereby incorporated by reference.

BACKGROUND OF THE INVENTION

The present invention relates to an assay method and a kit for an assay employing a sensor chip for a fluorescent measuring apparatus utilizing a surface plasmon-field enhanced Fluorescence Spectrometry.

A surface plasmon-field enhanced Fluorescence Spectrometry (hereafter, merely referred to as "SPFS") is a method capable of detecting an extremely small amount and/or extremely low concentration of analytes by efficiently exciting fluorescent dyes to label analytes (analysis target material) captured in the vicinity of a metal film by utilizing plasmon resonance which is increased to some tens of times to some hundreds of times by resonance between surface plasmon and evanescent wave which is transmitted through a metal layer when the surface of the metal layer formed on a dielectric substance is irradiated with exciting light such as laser light on the condition that total-reflection decrement is caused.

A sensor base plate used for such SPFS is described in Patent document 1. Patent document 1 discloses a sensor unit 100 as shown in FIG. 2, and the sensor unit 100 includes a transparent plate made of glass, plastics, or other transparent material; a metal film formed on one side of this plate by sputtering; a dextran layer (dextran film) bonded with this metal film, and ligands (antibodies) bonded with this dextran film. These ligands cause interaction (antigen-antibody reaction) with specific bio molecules (for example, antigens) which exist in a sample liquid, and Patent document 1 teaches about implementation of fluorescence measurement by utilization of SPFS with variable angle inner total reflection fluorescence.

In this connection, in Patent document 1, as mentioned above, analytes are detected using an antigen-antibody reaction. However, in the antigen-antibody reaction described in Patent document 1, there is a problem that immune reaction between antibodies and antigens is not yet enough. Generally, enhancement of the reactivity of the immune reaction between antibodies and antigens enhances assay light emission signal to be detected in proportion to the enhancement, thereby improving the reactivity between antibodies and antigens.

However, in proportion to the improvement of the immune reaction between antibodies and antigens, nonspecific reaction is also enhanced so as to increase assay noise signals which is a noise component. As a result, the measurement sensibility of analytes is not improved. Then, in a method disclosed in Patent document 2, in order to increase the measurement sensibility by suppressing increase of the assay noise signals, antibodies or antigens are mixed with both polyethylene glycols and urea, and antibodies and antigens are made to react with each other under the coexistence of these polyethylene glycols and urea.

Patent document 1: Japanese Patent No. 3294605 official report

Patent document 2: Japanese Unexamined Patent Publication No. 2010-145202 official report However, it turned out that although an antigen-antibody reaction with a mixture of polyethylene glycols and urea as described in Patent document 2 improves the measurement sensitivity as compared with conventional method, this technique even which is diverted to SPFS is insufficient to realize high accuracy detection for an extremely small amount and/or extremely low concentration of analytes, and the increase of S (assay light emission signal)/N (assay noise signal) ratio (measurement sensitivity) being a ratio of assay light emission signals to assay noise signals is restrictive. Further, as described in Patent document 2, in the embodiment that polyethylene glycol is mixed in the liquid, its concentration is limited. That is, for example, if polyethylene glycol is mixed in a liquid with extremely high concentration, the viscosity of the liquid becomes high too much, so that reactivity is lowered, and S (assay light emission signal) is decreased.

SUMMARY OF THE INVENTION

In view of the problems of the above conventional technologies, an object of the present invention is to provide an assay method and a kit for an assay employing a sensor chip for a fluorescent measuring apparatus utilizing a surface plasmon-field enhanced Fluorescence Spectrometry, which can improve S/N ratio more than conventional technologies.

The above object can be attained by the following methods.
(1) An assay method with use of a sensor chip which includes a metal member, a self-assembled monolayer (SAM), and ligands on a support, and is configured to be used for a fluorescence measuring apparatus with utilization of a surface plasmon-field enhanced Fluorescence Spectrometry, comprising the steps of:
forming a hydrophilic high molecule layer on the self-assembled monolayer in the sensor chip;
immobilizing the ligands at least one of in the hydrophilic high molecule layer and on the surface of the hydrophilic high molecule layer; and
bringing a moisturizer in contact with the hydrophilic high molecule layer.
(2) In the assay method described in Item (1), the hydrophilic high molecule layer contains hydrophilic high molecules in an amount of 0.001 ng/mm$^2$ or more and 30 ng/mm$^2$ or less.
(3) In the assay method described in Item (1), the hydrophilic high molecule layer contains high molecules in an amount of 0.2 ng/mm$^2$ or more and 6 ng/mm$^2$ or less.
(4) In the assay method described in any of Items (1) to (3), the hydrophilic high molecule layer contains at least one kind of high molecules selected from a group consisting of polysaccharide, polyethylene glycol, polyacrylic acid, and polymethacrylic acid.
(5) In the assay method described in Item (4), the polysaccharide is dextran or dextran derivative.
(6) In the assay method described in Item (5), the polysaccharide is carboxy methyl dextran.
(7) In the assay method described in any of Items (1) to (6), the moisturizer is at least one kind of material selected from a group consisting of urea, ethylene glycol, glycerin, ammonium lactate, pyrrolidone carboxylate, diol, lactic acid, hyaluronic acid, and chondroitin sulfate.
(8) In the assay method described in any one of Items (1) to (7), the moisturizer is at least one kind of material selected from a group consisting of urea, ethylene glycol, glycerin, and ammonium lactate.

(9) In the assay method described in any one of Items (1) to (8), the hydrophilic high molecule layer has an average layer thickness of 3 nm or more and 130 nm or less.
(10) In the assay method described in any one of Items (1) to (9), the hydrophilic high molecule layer has an average layer thickness of 50 nm or more and 100 mm or less.
(11) In the assay method described in any one of Items (1) to (10), the moisturizer has a rehydration sample moisture content of 40 to 200% by Riviere method.
(12) In the assay method described in any one of Items (1) to (11), the ligands are immobilized in the hydrophilic high molecule layer, and the immobilized ligands are 10 femto-mol/cm$^2$ or more and 100 pico-mol/cm$^2$ or less.
(13) In the assay method described in any one of Items (1) to (12), the moisturizer is added preliminarily into a liquid containing analytes, and the liquid containing the analytes and the moisturizer is brought in contact with the hydrophilic high molecule layer so that the moisturizer is brought in contact with the hydrophilic high molecule layer.
(14) In the assay method described in Item (13), the moisturizer has a concentration of 5 to 30% in the liquid containing the analytes and the moisturizer.
(15) In the assay method described in any one of Items (1) to (12), the moisturizer is added preliminarily into a cleaning liquid to clean an inside of the sensor chip before a liquid containing analyte is brought in contact with the ligands, and the cleaning liquid containing the moisturizer is brought in contact with the hydrophilic high molecule layer so that the moisturizer is brought in contact with the hydrophilic high molecule layer.
(16) In the assay method described in Item (15), the moisturizer has a concentration of 5 to 30% in the cleaning liquid containing the moisturizer.
(17) In the assay method described in any one of Items (1) to (16), the support is a transparent support.
(18) A kit for an assay for use in the assay method described in any one of Items (1) to (17), comprising:
a sensor chip which includes a metal member, a self-assembled monolayer (SAM), and a hydrophilic high molecule layer on a support, and is configured to be used for a fluorescence measuring apparatus; and
a moisturizer.
(19) In the kit for an assay, described in Item (18), the hydrophilic high molecule layer has a dried film thickness of 1 mu or more and 50 nm or less.

With the assay method and the kit for an assay according to the present invention, S/N ratio can improved so that a high sensitivity detection of analytes than conventional technologies can be realized.

DETAILED DESCRIPTION OF THE PREFERRED EMBODIMENT

Figure 1:
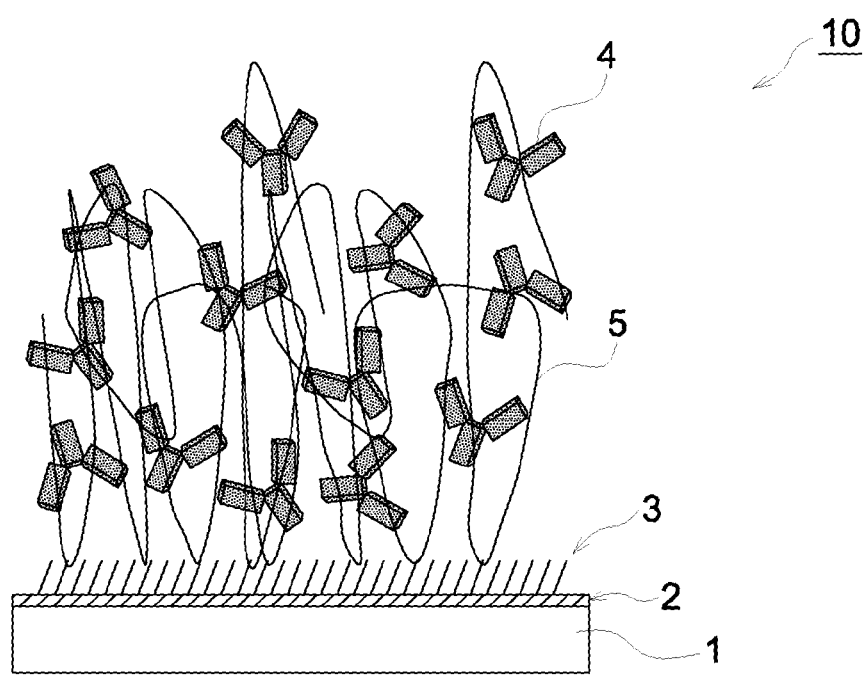
FIG. 1 is a longitudinal cross sectional diagram schematically showing one desirable embodiment of a sensor chip for a fluorescence measuring apparatus using SPFS according to the present invention.
Figure 2:
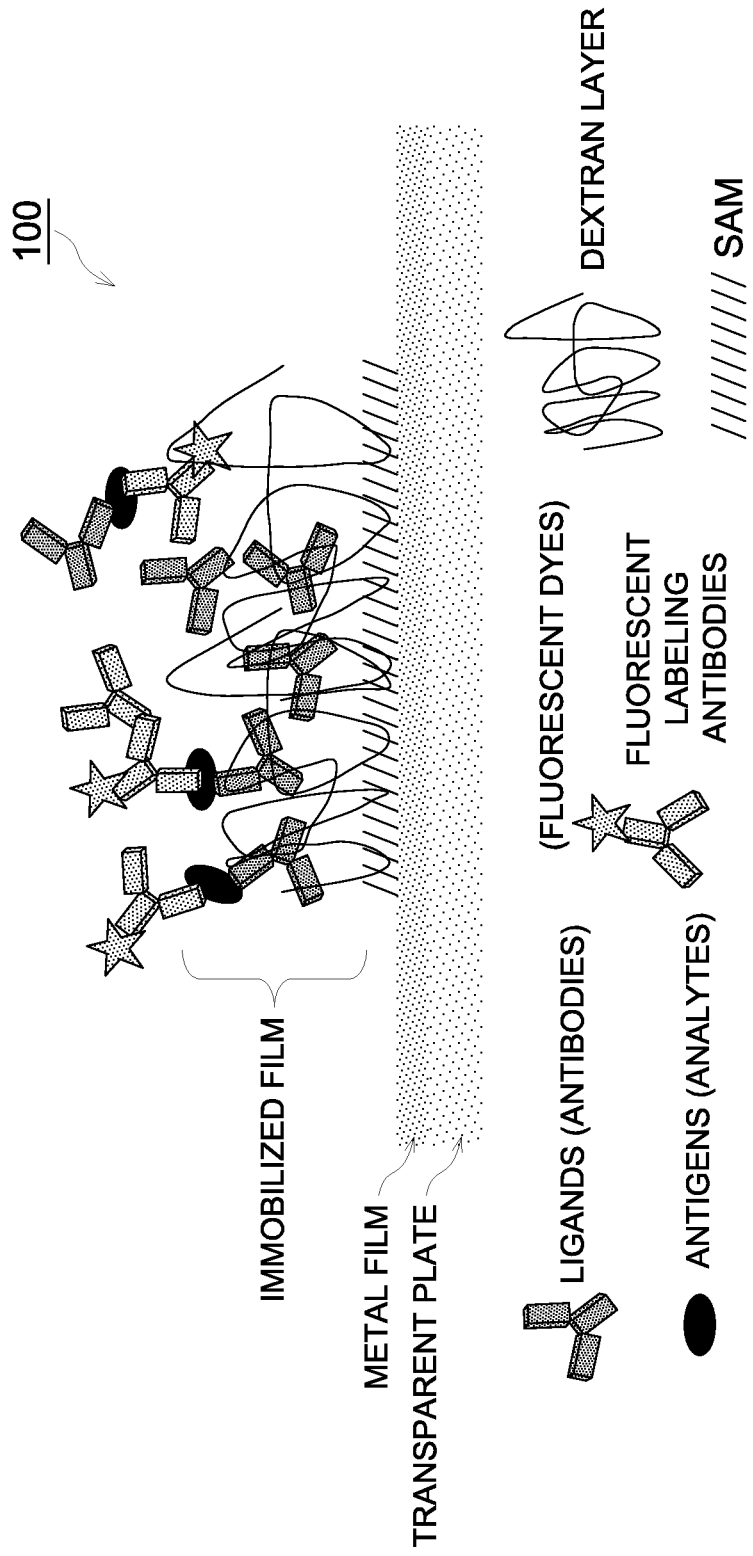
FIG. 2 is a longitudinal cross sectional diagram showing a sensor chip disclosed in Patent document 1.

The present invention is characterized in an assay method which uses a sensor chip which includes a hydrophilic high molecule layer formed on a self-assembled monolayer (SAM) and is used for a fluorescence measuring apparatus utilizing SPFS, and causes a mutual action (preferably, an antigen-antibody reaction) between ligands and analytes by bringing a moisturizer in contact with the hydrophilic high molecule layer in which and/or on the outer surface of which the ligands are immobilized. In the preferable embodiment of the present invention, with such an embodiment, the reactivity of immune reaction utilizing an antigen-antibody reaction can be enhanced dramatically. Furthermore, S/N ratio can be improved without being limited in terms of the amount of hydrophilic high molecules.

In an embodiment in which an antigen-antibody reaction is conducted by mixing hydrophilic high molecules in a liquid, the concentration of the hydrophilic high molecules is limited. Since a liquid in which the high concentration of hydrophilic high molecules is mixed causes precipitation of protein, an antigen-antibody reaction is influenced by the precipitation of protein so that the reproducibility of the measurement result is lost, and the repeatability of a measurement results is lost or the reactivity of N (assay noise signal) also improves simultaneously with the improvement in S (assay light emission signal). If the liquid is made more high concentration, as mentioned above, the liquid becomes a high viscosity liquid, and S (assay light emission signal) is lowered.

Thus, in the embodiment in which an antigen-antibody reaction is conducted by mixing hydrophilic high molecules in a liquid, if S/N ratio is made to improve more, the concentration of hydrophilic high molecules is limited. That is, even if the concentration of hydrophilic high molecules is made high, the improvement of SN ratio is limited.

In contrast, in the present invention, hydrophilic high molecules are not mixed in a liquid, and hydrophilic high molecules are used as a layer. Accordingly, hydrophilic high molecules can be used without being limited in terms of the amount (concentration, a density, and the like) of hydrophilic high molecules. As a result, as compared with conventional technologies, the value of S (assay light emission signal) is increased, so that high SN ration can be acquired.

As a mechanism, the following may be considered.

If a moisturizer is added to hydrophilic high molecules which form a hydrophilic high molecule layer, a hydration layer is formed in the vicinity of the hydrophilic high molecules by interaction between them. Namely, by use of hydrophilic high molecules as an antibody solid phase support (hydrophilic high molecule layer) on a SAM, a hydration layer is formed in the vicinity of the antibody solid phase support at the time of addition of a moisturizer. This hydration layer is considered to promote hydrophobic interaction between biological substances. As a result, the reactivity of the immune reaction utilizing an antigen-antibody reaction can be enhanced dramatically.

Hereafter, explanation will be given concretely with regard to an assay method and a kit for an assay that employ a sensor chip for a fluorescent measuring apparatus utilizing SPFS of the present invention.

<Sensor Chip for a Fluorescent Measuring Apparatus Utilizing SPFS>

FIG. 1 shows one desirable embodiment of a sensor chip for a fluorescent measuring apparatus (hereafter, referred merely to a "sensor chip") which utilizes SPFS and is used for the present invention. As shown in FIG. 1, the sensor chip used for the present invention is provided with at least a metal member 2 (metal film mentioned later), a self-assembled monolayer (SAM) 3, and ligands 4 on a support 1, and includes a hydrophilic high molecule layer 5 on the SAM 3.

Although the hydrophilic high molecule layer 5 shown in FIG. 1 has a three dimensional structure, each one of hydrophilic high molecules forming the hydrophilic high molecule layer 5 may be immobilized on the support 1 in an approximately-vertical state or one hydrophilic high molecule such as dextran, may be immobilized on the support medium 1 at two or more places. The present invention is not limited to any one of the embodiments.

(Support)

As a support of the sensor chip, a transparent support is employed preferably. The reason why the transparent support is employed preferably as a support of the sensor chip is that a metal member described later is irradiated with light through this transparent support.

As long as the object of the present invention can be attained, the material of the transparent support is not limited specifically. For example, this transparent support may be made of glass, or may be made of plastics, such as polycarbonate [PC] and cycloolefin polymer [COP].

In the transparent support, a refractive index $[n_d]$ for "d" line (588 nm) is preferably 1.40 to 2.20, and a thickness is preferably 0.01 to 10 mm, and more preferably 0.5 to 5 mm. If the transparent support satisfies the above conditions, a (longitudinal×transverse) is not limited specifically.

As commercialized products of the material of the transparent support made of glass, from the viewpoints of optical characteristics and cleaning performance, it is preferable to employ "BK7" (refractive index $[n_d]$: 1.52) and "LaSFN9" (refractive index $[n_d]$: 1.85) which are manufactured by Schott Japan Corporation; "K-PSFn3" (refractive index $[n_d]$: 1.84), "K-LaSFn17" (refractive index $[n_d]$: 1.88), and "K-LaSFn22" (refractive index $[n_d]$: 1.90) which are manufactured by Sumita Optical Glass Inc.; and "S-LAL10" (refractive index $[n_d]$: 1.72) manufactured by Ohara Inc.

Before a metal member is formed in a surface of the support, it is desirable to clean the surface of the support by acid and/or plasma.

As cleaning treatment by acid, it is desirable to dip the support in hydrochloric acid with 0.001 to 1 M (mole)/liter for 1 to 3 hours.

As cleaning treatment by plasma, a method for dipping the support in a plasma dry cleaner ("PDC200" manufactured by Yamato Scientific Co., Ltd.) for 0.1 to 30 minutes may be employed.

(Metal Member)

The sensor chip includes a metal member on the support mentioned above. The metal member has a role to generate surface plasmon or localized plasmon by light irradiated from a light source. As the metal member, for example, a metal film or metal particles may be employed. It may be preferable to form the metal member as a metal film on the surface of an above-mentioned support. This metal film has a role to induce a surface plasmon with exciting light irradiated from a light source, and to excite a fluorescent dye efficiently.

The metal film formed on the surface of the support may be preferably composed of at least one kind of metals selected from a group consisting of gold, silver, copper, aluminum, platinum, and zinc, and more preferably composed of gold. The metal film may be composed of several alloys of the above metals, and the metal film may be a plurality of laminated layers. Such kinds of metals are stable for oxidation, and are preferable because electric field enhancement by plasmon resonance becomes large.

In the case where a support made of glass is used as the support, in order to bond more firmly the above metal film to the glass, it is preferable to form a thin film of chromium, a nickel chrome alloy, or titanium on the support of glass beforehand.

Examples of the methods forming the metal film on the support include a sputtering method, a vapor deposition method (a resistance heating vapor deposition method, an electron beam vapor deposition method, etc.), an electrolytic plating method, and an electroless plating method. From the viewpoint of easiness in adjustment of film forming conditions, it may be preferably to form a metal film by a sputtering method or a vapor deposition method. Further, the case where a thin film of chromium, a nickel chrome alloy, or titanium is formed on the support is the same with this case of the metal film.

The thickness of the metal film is preferably 5 to 500 nm in the case of gold, 5 to 500 nm in the case of silver, 5 to 500 nm in the case of aluminum, 5 to 500 nm in the case of copper, 5 to 500 mu in the case of platinum, and 5 to 500 nm in the case of alloy of these metals, and the thickness of chromium is preferably 1 to 20 nm.

From the viewpoint of the effect of electric field enhancement, the thickness of the metal film is more preferably 20 to 70 nm in the case of gold, 20 to 70 nm in the case of silver, 10 to 50 nm in the case of aluminum, 20 to 70 nm in the case of copper, 20 to 70 nm in the case of platinum, and 10 to 70 nm in the case of alloy of these metals, and the thickness of chromium is more preferably 1 to 3 nm.

If the thickness of the metal film is within the above range, since surface Plasmon occurs easily, it is suitable. Further, if the metal film has such a thickness, an area (longitudinal× transverse) is not limited specifically.

On the other hand, in the case where metal particles are used as the metal member, it is possible to induce localized plasmon. As long as particles capable of inducing Plasmon can be prepared, the kind of metals used as the metal particles is not limited. However, at least one kind of a metal selected from a group consisting of gold, silver, copper, aluminum, platinum, and zinc or an alloy of two or more kinds of those metals may be preferably employed. As long as the particle size of a metal particle is within a range in which localized Plasmon can be caused, the particle size of the metal particles is not limited. However, the particle size of a metal particle is preferably 10 to 100 nm, and it is preferable to utilize a group of metal particles having an average particle size existing within such a range.

For example, the metal particles can be used in the state that the metal particles are dispersed on the support mentioned above.

(Self-Assembled Monolayer (SAM))

SAM (Self-Assembled Monolayer) is formed on another surface of the metal member which is not in contact with the support, as a stage to make a hydrophilic high molecule layer into a solid phase and for the purpose of prevention of metal quenching of fluorescence molecules at the time of fluorescence photometry.

As a mono-molecule which forms SAM, carboxy alkane thiol (for example, available from Dojin Chemical Laboratory Co., Ltd., Sigma-Aldrich Japan, Inc. and the like) with about 4 to 20 carbon atoms may be usually employed, and 10-carboxy-1-decan thiol may be more preferably employed. Carboxy alkane thiol with about 4 to 20 carbon atoms may be suitable, because SAM formed by use of it has little optical influence, that is, has characteristics such as high transparency, low refractive index, and thin film thickness.

The method for forming such SAM is not limited specifically, but a conventionally well-known method can be employed. Specific examples of the methods include a method of dipping a support on which a metal member is formed, in an ethanol solution containing 10-carboxy-1-decan thiol (manufactured by Dojin Chemical Laboratory Co., Ltd.). In this case, a thiol group included in 10-carboxy-1-deccan thiol bonds with a metal of a metal member so as to be immobilized, so that 10-carboxy-1-deccan thiol self-assembles on the surface of the metal member, whereby SAM is formed.

Before formation of SAM, "a spacer layer composed of dielectrics" may be formed on a metal member. In this case, if silane coupling agents include an ethoxy group (or methoxy group) which provides a silanol group [Si—OH] by hydrolysis, and a reactive group, such as an amino group, a glycidyl group, and a carboxyl group, at its one end, conventionally-know silane coupling agents may be employed as a monomolecule to form SAM.

As the dielectrics used for such "a spacer layer composed of dielectrics", various optically-transparent inorganic substances or synthetic polymers may be employed. Among them, dielectrics containing a silicon dioxide [$SiO_2$], a titanium dioxide [$TiO_2$], or an aluminum oxide [$Al_2O_3$] may be preferably employed, because it is excellent in chemical stability, manufacture stability and optical transparency.

The thickness of the spacer layer composed of dielectrics is usually 10 nm to 1 mm, preferably 30 nm or less from the viewpoint of resonance angle stability, and more preferably 10 to 20 nm. On the other hand, from the viewpoint of an electric field enhancement, it is preferably 200 nm to 1 mm, and from the viewpoint of the stability of an effect of an electric field enhancement, it is more preferably 400 nm to 1,600 nm.

Examples of methods for forming the spacer layer composed of dielectrics include a sputtering method, an electron beam vapor deposition method, a thermal vapor deposition method, a forming method with a chemical reaction by use of materials such as polysilazane, and a coating method with a spin coater.

(Hydrophilic High Molecule Layer)

The hydrophilic high molecule layer according to the present invention is formed another surface of the above SAM which is not in contact with the metal member, and has a two dimensional structure or three dimensional structure.

This "three-dimensional structure" means the structure of the hydrophilic high molecule layer which can extend the immobilization of ligands mentioned later even to a three-dimensional space separated from a surface of the support without limiting to a two dimensional structure on the surface of the support. In this way, by use of hydrophilic high molecules mentioned later as a layer, the hydrophilic high molecule layer according to the present invention can be used without being limited to an amount (concentration and density) of the hydrophilic high molecule. The high molecules of the hydrophilic high molecule layer according to the present invention mean compounds with a molecular weight of 5000 or more.

Such a hydrophilic high molecule layer preferably contains polyacrylic acid, polymethacrylic acid, and polysaccharide composed of at least one kind of monomers selected from a group consisting of monomers contained in glucose, carboxy methylated glucose, vinyl esters, acrylic esters, methacrylic acid esters, olefins, styrenes, crotonic acid esters, itaconic acid diesters, maleic acid diesters, fimaric acid diesters, allyl compounds, vinyl ethers and vinyl ketones. The polysaccharide preferably includes hydrophilic high molecules, such as dextran and dextran derivatives. A hydrophilic high molecule layer composed of dextran such as carboxy methyl dextran [CMD] may be specifically suitable from the view points of improvement of bio-compatibility, improvement of suppression properties of nonspecific adsorption reaction, and acquisition of high hydrophilia.

The molecular weight of CMD is preferably 1 kDa or more and 5,000 kDa or less, and more preferably 4 kDa or more and 1,000 kDa or less.

Although the density (mass per a unit area of a hydrophilic high molecule layer formed on SAM) of high molecules of a hydrophilic high molecule layer may be suitably adjusted in accordance with the kind of used high molecules and a layer forming method, the density may be 0.001 $ng/mm^2$ or more and 30 $ng/mm^2$ or less as one example. Further, depending on the film thickness of a hydrophilic high molecule layer, it is preferable to satisfy a range of 0.2 $ng/mm^2$ or more to 6 $ng/mm^2$ or less. Examples of methods for adjusting the density include a method for adjusting the density by adjusting the concentration of high molecules in a high molecule-containing liquid to form a hydrophilic high molecule layer, and a method for adjusting the density by adjusting the molecular weight of high molecules used for hydrophilic high molecules. Particularly, in a hydrophilic high molecule layer containing dextran or a dextran derivative, it is desirable for high molecules to satisfy a density within this range. If an assay is conducted by use of a sensor chip in which hydrophilic high molecules are solid-phased with a density being within the above range on the above SAM, it is suitable, because assay light emission signals are stabilized and increases.

The average film thickness of a hydrophilic high molecule layer can be suitably adjusted in accordance with the kind of high molecules to be used and the density of a layer. For example, the average film thickness may be 3 nm or more and 300 nm or less, preferably in a range of 3 nm or more and 130 nm or less, and more preferably in a range of 50 nm or more and 100 nm or less. The film thickness may be measured by use of an atomic force microscope [AFM]. If the average film thickness of a hydrophilic high molecule layer is within such a range, it is suitable, because assay fluorescence signals are stabilized and increases. The above range of the average film thickness is an average film thickness in a liquid such as an analyte liquid.

As a matter of course, the hydrophilic high molecule layer of the present invention has a role as a stage at the time of secure ligands to a metal member. In addition, in a reaction with a moisturizer mentioned later, in the state that the hydrophilic high molecule layer is formed on SAM, the hydrophilic high molecule layer reacts with the moisturizer, whereby the reactivity of an immune reaction utilizing an antigen-antibody reaction can be rapidly intensified. Although methods for forming a hydrophilic high molecule layer are not limited in particular, for example, a method for forming by dipping a substrate, on which a hydrophilic high molecule layer is desired to be formed, in a high molecule-containing liquid for a predetermined time, and a method for coating by use of a spin coater and sintering (for example, 70 to 80° C.) may be employed.

(Ligand)

The ligands are used for the purpose of securing (capturing) analytes in a specimen, and are immobilized in the above-mentioned hydrophilic high molecule layer. In the case where the hydrophilic high molecule layer is a two dimensional structure, the ligands are immobilized on the outer surface of the hydrophilic high molecule layer, and in the case where the hydrophilic high molecule layer is a three dimensional structure, the ligands are immobilized in the inside and/or on the outer surface of the hydrophilic high molecule layer. Generally, in the case where the hydrophilic high molecule layer is a three dimensional structure, many of the ligands are immobilized by being dispersed in the three dimensional structure of the hydrophilic high molecule layer.

In this specification, in order to discriminate between the above ligands, that is, ligands immobilized in a hydrophilic high molecule layer so as to catch analytes in a specimen and ligands used for conjugation with fluorescent dyes, the ligands immobilized in a hydrophilic high molecule layer are hereafter referred to as first ligands, and the ligands used for conjugation with fluorescent dyes are hereafter referred to as second ligands. Molecules or molecular fragments used at the first ligands and the second ligands may be the same to each other or may be different from each othere.

The first ligands are molecules or molecular fragments both of which specifically recognize (or are recognized) analytes contained in a specimen and can join with the analytes. Examples of such "molecules" or "molecular fragments" include, without being limited thereto, nucleic acid (i.e., DNA, RNA, polynucleotide, oligonucleotide, PNA (peptide nucleic acid), etc. which may be a single strand or may be a double strand), nucleoside, nucleotides and those modification molecules); protein (polypeptide, oligopeptide, etc.); amino acid (including modification amino acid); saccharinity (oligosaccharide, a polysaccharide, sugar chain, etc.), lipid or their modification molecules and complex.

Examples of "protein", include antibody, and the like, and specific examples include an anti-α fetoprotein [APP] monoclonal antibody (available from Japan Clinical Laboratories, Inc.), an anticarcinoembryonic antigen [CEA] monoclonal antibody, an anti-CA19-9 monoclonal antibody, an anti-PSA monoclonal antibody.

In this specification, the term "antibody" implies a polyclonal antibody, a monoclonal antibody, an antibody obtained by gene recombination, and an antibody fragment.

Examples of methods for immobilizing the first ligands in a hydrophilic high molecule layer, include a method for active-esterizing a carboxyl group included in high molecules including a reactive functional group, such as carboxy methyl dextran [CMD] by water-soluble carbodiimide [WSC] (for example, 1-ethyl-3-(3-dimethylamino propyl) carbodiimide hydrochloride [EDC] etc.) and N-hydroxysuccinic acid imide [NHS], and making such active-esterized carboxyl group and an amino group included in the first ligands to cause a dehydration reaction by use of water-soluble carbodiimide, thereby immobilizing the first ligands.

After immobilization of the first ligand, in order to prevent a specimen mentioned later from nonspecifically sticking to a sensor chip, it is desirable to treat the surface of the sensor chip with a blocking agent such as a bovine serum albumin [BSA].

The density of ligands immobilized in the above hydrophilic high molecule layer is preferably 1 femto mol/cm$^2$ or more and 1 nano mol/cm$^2$ or less, and more preferably 10 femto mol/cm$^2$ or more and 100 pico mol/cm$^2$ or less. When the density of ligands is within the above range, it is suitable, because the signal intensity of assay fluorescence signals becomes large.

(Moisturizer)

The moisturizer is a material with a function to reduce a nonspecific reaction (assay noise signal). Examples of the moisturizer include urea, ethylene glycol (EG), glycerin, ammonium lactate, pyrrolidone carboxylic acid, diol, lactic acid, hyaluronic acid, and chondroitin sulfate. The rehydration specimen moisture content of the moisturizer by Riviere method (reference: M. Riviere et al., Water retention of treated stratum corneum measured by a coupling method: thermal desorption-mass spectrometry, International Journal of Cosmetic Science 17, 165-172 (1995) is preferably within a range of 40 to 200%. Examples of this moisturizer include urea, ethylene glycol (EG), glycerin, Lectil, and ammonium lactate. The above moisturizers may be used solely, or in combination of two kinds or more.

It may be permissible for the moisturizer to merely coexist with the hydrophilic high molecule layer mentioned above at the time of start of an antigen-antibody reaction, and if the moisturizer comes in contact with the hydrophilic high molecule layer until the same time with the time of action of antigen-antibody reaction, the contact is not limited in terms of timing and sequential order.

Examples of the method of bringing the moisturize in contact with the hydrophilic high molecule layer include a method of mixing the moisturizer with an analyte liquid mentioned later and bringing the mixed analyte liquid in contact with the hydrophilic high molecule layer, and a method of mixing the moisturizer with a later-mentioned cleaning liquid to clean the inside of a sensor chip and bringing the mixed cleaning liquid in contact with the hydrophilic high molecule layer. However, a liquid containing only the moisturizer or a liquid containing the moisturizer may be brought in contact with the hydrophilic high molecule layer.

As for the moisturizer, the rehydration specimen moisture content of the moisturizer by the above Riviere method is preferably 40 to 200%. If the rehydration specimen moisture content of the moisturizer is 40 to 200%, a hydration layer is easily formed on a solid phase antibody. Further, with this, since an antigen-antibody reaction is promoted, it is desirable.

Moreover, in the case where the moisturizer is contained in a liquid, the concentration of the moisturizer is preferably 5 to 30%.

<Assay>

The assay of the present invention is characterized by including at least a process of bringing a moisturizer in contact with a sensor chip in which a hydrophilic high molecule layer is formed on a SAM.

In detail, the assay may include the following processes (a) to (d), and further may include cleaning processes (1) and (2) if needed.

Process (a): a process of bringing an analyte liquid in contact with the sensor chip of the present invention Process (b): a process of making the sensor chip acquired through the process (a) to react with a conjugate material of fluorescent dyes and second ligands which may be the same with or different from first ligands contained in this sensor chip Process (c): a process of irradiating laser light via a prism to another surface, on which the above metal member is not formed, of the support of the sensor chip acquired through the process (b) and measuring an amount of fluorescence emitted from the fluorescent dye excited with the irradiated laser light Process (d): a process of calculating an amount of analyte contained in the analyte liquid from the measurement results obtained by the process (c)

Cleaning process (1): a process of cleaning the inside of the sensor chip acquired through the above-mentioned process (a) with a cleaning liquid Cleaning process (2): a process of cleaning the inside of the sensor chip acquired through the above-mentioned process (b) with a cleaning liquid In the present invention, it is desirable that a moisturizer is mixed in at least one of the analyte liquid in the above process (a) and the cleaning liquid in the above cleaning process (1).

[Process (a)]

The process (a) is a process of bring contacts an analyte liquid in contact with the first ligands immobilized in the hydrophilic high molecule layer.

(Analyte Liquid)

In the present invention, the term "analyte liquid" means a liquid containing various analytes to be deemed as measurement objects.

As long as liquids contain analytes, an analyte liquid may be any one of the liquids. However, examples of the analyte liquid include specimens, and examples of the specimens include blood (blood serum and blood plasma), urine, a nasal aperture liquid, saliva, feces, coelomic fluid (spinal fluid, ascites, pleural effusion, etc.). The specimens may be used by being diluted suitably with a desired solvent, buffer solution, and the like. Among the above specimens, blood, urine, a nasal aperture liquid, and saliva may be desirable. These specimens may be used solely, or may be used in combination of two or more kinds.

(Analyte)

In the present invention, the term "analyte" means molecules or molecule fractions both of which are specifically recognized by the first ligands (or specifically recognize the first ligands) immobilized in the hydrophilic high molecule layer and can join with them. Examples of such "molecules" or "molecular fragments" include nucleic acid (i.e., DNA, RNA, polynucleotide, oligonucleotide, PNA (peptide nucleic acid), etc. which may be a single strand or may be a double strand), nucleoside, nucleotides and those modification molecules); protein (polypeptide, oligopeptide, etc.); amino acid (including modification amino acid); saccharinity (oligosaccharide, a polysaccharide, sugar chain, etc.), lipid or their modification molecules and complex. Specific examples include, without being limited thereto, tumor markers, such as AFP (α fetoprotein) and carcinoembryonic antigen, signal transmitting materials, and hormone.

(Contact of an Analyte Liquid)

It is desirable that a flow passage is formed in a sensor chip, and at least a part of the flow passage includes a metal member on a support and a hydrophilic high molecule layer and first ligands on a SAM. A preferable embodiment is that when an analyte liquid is made to flow through the flow passage and the first ligands are dipped in the analyte liquid, analytes are brought in contact with the first ligands.

The configuration of the "flow passage" may be shaped in a square tube (pipe), or a round tube (pipe). A reaction and measurement section which makes analytes and first ligands to join with each other and measures fluorescence is preferably shaped in a square tube. A flow passage portion which is other than the above section and used only for feeding a liquid such as a medical liquid is preferably shaped in a round tube.

Examples of material of members constituting external walls of a sensor chip, for example, portions (support) corresponding to the reaction and measurement section of the members and a flow passage top plate in the case where the sensor chip is constituted by a flow passage base plate and a flow passage top plate, include a resin composed of homopolymers or copolymers which contains methyl methacrylate, styrene, and the like as raw materials, or polyolefines, such as polyethylene, and examples pf materials of flow passage portions, include silicone rubber, Teflon (registered trademark), and a resin composed of polymers such as polyethylene and polypropylene.

In the reaction and measurement section, each of height and width of the cross section of the flow passage is preferably about 100 nm to 1 mm from the viewpoints of increasing of contacting efficiency with analytes and shortening of dispersion distance.

As methods for forming a flow passage in a sensor chip, in a small-scale lot (laboratory level), the following method is preferable. First, on a surface side on which a metal film is formed, for example, as a metal member of the sensor chip, a sheet which is made of poly-dimethyl siloxane [PDMS] and has a flow passage with a height of 0.5 mm is bonded with pressure so as to surround a portion where the metal thin film of the sensor chip is formed. Next, the sheet made of poly-dimethyl siloxane [PDMS] is secured to the sensor chip with a securing member such as screws.

As methods for forming a flow passage in a sensor chip, in a large-scale lot (factory level) manufactured industrially, the following methods may be employed. According to one method, an integrally-molded plastics product corresponding to a flow passage base plate and a flow passage top plate is formed in a sensor chip. According to another method, a flow passage base plate is formed on a separately-produced support on which a metal film is formed, and on the surface of the metal thin film (preferably, a spacer layer composed of dielectric substance), a SAM and a hydrophilic high molecule layer are formed and ligands are immobilized. Thereafter, the sensor chip in which the flow passage base plate is formed is covered with an integrally-molded plastics product corresponding to a flow passage top plate.

Examples of solvents used for diluting analytes as an analyte liquid to be fed to a flow passage, include, without being specifically limited thereto, a phosphate buffered saline [PBS], a Tris buffered saline solution [TBS], a HEPES buffered saline [HBS].

It is desirable to circulate the fed analyte liquid through the flow passage in order to make the first ligands to trap many analytes. At this time, the temperature of the analyte liquid and the time of circulation may be different depending on the kind of specimens. However, the temperature and the time are, without being specifically limited thereto, usually 20 to 40° C. and 1 to 60 minutes, and preferably 37° C. and 5 to 15 minutes.

When the analyte liquid (specimen) is fed to a flow passage, the initial concentration (concentration before feeding) of analytes contained in this analyte liquid may be 100 μg/ml to 0.001 pg/ml.

The total amount of the analyte liquid fed to a flow passage is usually 0.001 to 20 ml, and preferably 0.1 to 1 ml.

The flow rate of the analyte liquid fed to a flow passage is usually 1 to 50,000 μL/min, and preferably 5,000 to 10,000 microl/min.

[Cleaning Process]

The cleaning process includes a cleaning process (1) which cleans the inside of a sensor chip with a cleaning liquid after the above-mentioned process (a), and a cleaning process (2) which cleans the inside of the sensor chip with a cleaning liquid after the above-mentioned process (b).

As a desirable embodiment of the present invention, a moisturizer to be brought in contact with a hydrophilic high molecule layer is used by being mixed in the analyte liquid in the above process (a), by being mixed in the cleaning liquid in the cleaning process (1), or by being mixed in both the analyte liquid and the cleaning liquid.

Preferable examples of the cleaning liquids used in these cleaning processes (1) and (2), include a cleaning liquid in which surface active agents, such as Tween20 and TritonX100 are dissolved in a content of preferably 0.00001 to 1 mass % in the same solvent or buffer solution as that used in the processes (a) and (b) and a cleaning liquid in which salts such as sodium chloride, and potassium chloride are dissolved in an amount of 10 to 500 mM in the above solvent or buffer solution. Alternatively, a low pH buffer solution, for example, 10 mM Glycine HCl with a pH of 1.5 to 4.0 may be used as the cleaning liquid.

It is desirable that the temperature and flow rate of the cleaning liquid in the cleaning process are the same temperature and the same flow rate as those at the time of feeding of the analyte liquid in the above-mentioned process (a).

The cleaning process (the cleaning time with the cleaning liquid) is usually for 0.5 to 180 minutes, and preferably for 5 to 60 minutes.

[Process (b)]

The process (b) is a process of making the sensor chip to react with a conjugate material of a fluorescent dye and ligands (second ligands) which may be the same with or different from the ligands (first ligands) immobilized in the hydrophilic high molecule layer after the process (a), preferably, after the cleaning process (1).

(Fluorescent Dye)

The "fluorescent dye" is a collective term for materials which emits fluorescence by being irradiated with predetermined excitation light, or by being excited with utilization of an electric field effect, and the "fluorescence" includes various kinds of light emission, such as phosphorescence.

Unless fluorescent dyes are not quenched thoroughly due to light absorption by the metal member, any one of well-known fluorescent dyes may be used as the fluorescent dyes used in the present invention without being limited specifically in terms of kind. Preferable fluorescent dyes make it possible to use a fluorescent measuring device equipped with a filter rather than a monochrome colorimeter [monochromometer], and have large Stokes shift which increases detection efficiency.

Examples of the fluorescent dyes include fluorescent dyes of a fluorescin family (manufactured by Inegrated DNA Technologies Inc.), fluorescent dyes of polyhalo fluorescin family (manufactured by Applied Biosystems Japan, Co., Ltd.), fluorescent dyes of a hexachloro fluorescin family (manufactured by Applied Biosystems Japan, Co., Ltd.), fluorescent dyes of a cumarin family (manufactured by Invitrogen Corporation), fluorescent dyes of a rhodamine family (manufactured by GE Health care Bioscience Corporation), fluorescent dyes of a cyanine family, fluorescent dyes of an India carbocyanine family, fluorescent dyes of an oxazin family, fluorescent dyes of a thiazin family, fluorescent dyes of a squaraine family, fluorescent dyes of a chelation lanthanides family, fluorescent dyes of BODIPY (Registered Trademark) family (manufactured by Invitrogen Corporation), fluorescent dyes of a naphthalenesulfonic acid family, fluorescent dyes of a pyrene family, fluorescent dyes of a triphenylmethane family, and Alexa Fluor (Registered Trademark) dyeseries (manufactured by Invitrogen Corporation). Further, examples include fluorescent dyes disclosed in U.S. Pat. Nos. 6,406,297, 6,221,604, 5,994,063, 5,808,044, 5,880,287, 5,556,959, and U.S. Pat. No. 5,135,717.

The absorption wavelength (nm) and emission wavelength (nm) of typical fluorescent dyes contained in these families are shown in Table 1.

TABLE 1

| Fluorescent dye | Family | Absorption wavelength (nm) | Emission wavelength (nm) |
| --- | --- | --- | --- |
| Aminomethyl coumarin; AMCA | Coumarin | 350 | 450 |
| Cy2 (Registered Trademark) | Cyanine | 492 | 510 |
| Fluorescein Isothiocyanate; FITC | Fluorescein | 492 | 520 |
| Cy3 (Registered Trademark) | India carbocyanine | 550 | 570 |

TABLE 1-continued

| Fluorescent dye | Family | Absorption wavelength (nm) | Emission wavelength (nm) |
| --- | --- | --- | --- |
| Tetramethyl Rhodamine Isothiocyanate; TRITC | Rhodamine | 550 | 570 |
| Rhodamine Red-X; RRX | | 570 | 590 |
| Texas Red; TR | | 596 | 620 |
| Cy5 (Registered Trademark) | Cyanine | 650 | 670 |
| Alexa Fluor (Registered Trademark) 647 | Cyanine | 650 | 665 |

Further, the fluorescent dyes are not limited to the above-mentioned organic fluorescent dyes. For example, the fluorescent dyes of rare earth complex systems, such as Eu and Tb, may also be used. The rare earth complex has generally a large difference in wavelength between an excitation wave length (about 310 to 340 nm) and an emission wave length (near 615 nm in an Eu complex, and near 545 nm in an Tb complex), and are characterized in that the life time of fluorescence is as long as some hundreds of microseconds or more. Examples of the commercially-available fluorescent dyes of the rare earth complex system include ATBTA-Eu3+.

In the present invention, it is desirable to use the fluorescent dyes which have a maximum fluorescence wavelength in a wavelength region where light absorption by the metal contained in the metal member is small at the time of measurement of fluorescence mentioned later. For example, in the case where gold is used as the metal member, in order to suppress the influence of light absorption by a golden member to the minimum, it is desirable to use fluorescent dyes which have a maximum fluorescence wavelength not less than 600 nm. Therefore, in this case, it is particularly desirable to use fluorescent dyes, such as Cy5, Alexa Fluor (Registered Trademark) 647, and the like which have a maximum fluorescence wavelength in a near infrared region. The use of such fluorescent dyes which have a maximum fluorescence wavelength in a near infrared region is useful in the point that the influence of light absorption by iron derived from blood corpuscle components in blood can be suppressed to the minimum in the case where blood is used as a specimen. On the other hand, in the case where silver is used as the metal member, it is desirable to use fluorescent dyes which have a maximum fluorescence wavelength of 400 nm or more.

These fluorescent dyes may be used solely with one kind, or in combination of two or more kinds.

(Conjugate of the Second Ligands and the Fluorescent Dyes)

As to the "conjugate of fluorescent dyes and ligands (second ligands) which may be the same with or different from ligands (first ligands) immobilized in the hydrophilic high molecule layer of the present invention", in the case where second antibodies are used as the second ligands, it is desirable that the conjugate can recognize analytes (target antigens) contained in a specimen and can join with the analytes.

The second ligands are ligands used for the purpose of performing labeling analytes with fluorescent dyes, and may be the same with or different from the first ligands as mentioned above. In this regard, in the case where the first antibodies used as the first ligands are polyclonal antibodies, the second antibodies used as the second ligands may be monoclonal antibodies or polyclonal antibodies. However, in the case where the first antibodies are monoclonal antibodies, it is desirable that the second antibodies are monoclonal antibodies which recognize epitopes which the first antibodies do not recognize, or polyclonal antibodies.

Further, a preferable embodiment is to use composite bodies in which second antibodies join with second analytes (competitive antigens; different from target antigens) which compete with analytes (target antigen) contained in an analyte liquid. Such an embodiment is preferable, because an amount of fluorescence (assay fluorescence signal) can be made to be proportional to an amount of target antigens.

Examples of methods for producing the conjugate material of the second ligands and the fluorescent dyes, include a method with which first, the fluorescent dyes are provided with carboxyl groups, the carboxyl groups are actively esterified by water-soluble carbodiimide [WSC] (for example, 1-ethyl-3-(3-dimethylamino propyl) carbodiimide hydrochloride [EDC], etc.) and N-hydroxysuccinic acid imide [NHS], and then the actively-esterified carboxyl groups and amino groups included in the second ligands are made to cause dehydration reaction by use of water-soluble carbodiimide so as to be immobilized; a method by which the second ligands and the fluorescent dyes each of which includes isothiocyanate and amino groups are made to react with each other so as to be immobilized; a method by which the second ligands and the fluorescent dyes each of which includes sulfonyl halide and amino groups are made to react with each other so as to be immobilized; a method by which the second ligands and the fluorescent dyes each of which includes iodoacetamide and thiol groups are made to react with each other so as to be immobilized; and a method by which biotinylated fluorescent dyes and streptoavidinized second ligands (or, streptoavidinized fluorescent dyes and biotinylated second ligands) are made to react with each other so as to be immobilized.

When a liquid containing the thus-produced conjugate material of the second ligands and the fluorescent dyes is fed to a sensor chip so as to cause reaction, the concentration of the liquid to be fed is preferably 0.001 to 10,000 μg/ml, and more preferably 1 to 1,000 μg/ml.

The temperature and flow rate of this liquid and the time (liquid feeding time) at the time of feeding of the liquid are the same temperature, the same flow rate, and the same time as those in the case of the above-mentioned process (a).

[Process (c)]

The process (c) is a process of irradiating laser light via a prism to another surface, on which the above metal member is not formed, of the support of the sensor chip acquired through the process (b) and measuring an amount of fluorescence emitted from the fluorescent dyes excited with the irradiated laser light.

(Optical System)

If light sources for irradiating light at the time of measurement of an amount of fluorescence can be make a metal member to cause plasmon excitation, the light sources are not limited specifically. However, it is desirable to use laser light as a light source in the point of unity of wavelength distribution and strength of light energy. It is desirable to adjust energy and an amount of photon just before entering a prism by making laser light to pass through an optical filter.

Irradiation of laser light causes surface plasmon on the surface of a metal member on the total-reflection decrement condition [ATR]. The fluorescent dyes are excited by photons an amount which is increased some often times to some of hundred times the amount of irradiated photons by the electric field enhancement effect of the surface Plasmon. In this regard, the increased amount by the electric field enhancement effect depends on the refractive index of a support, the metal kind of a metal member, and the film thickness of the metal member. Usually, in the case of gold, the increased amount becomes 10 to 20 times.

In the fluorescent dyes, electrons in molecules are excited by light absorption, the electrons move to the first electron exciting state for a short time, and when the electrons move back from this state (level) toward the ground state, the fluorescent dyes emit fluorescence with a wave length corresponding to an energy difference at that time.

Examples of the light sources of "laser light" include LD with a wavelength of 200 to 900 nm or 0.001 to 1000 mW, and a semiconductor laser with a wavelength of 230 to 800 nm (a resonance wave length is determined in accordace with a metal kind used for the metal member) or 0.01 to 100 mW.

The "prism" is used for the purpose of make laser light to enter the metal member efficiently via various filters, such as an optical filter, a polarization filter, and a cut filter which are used if needed, and has preferably the same refractive index as that of the transparent support. In the present invention, since various prisms capable of setting the total-reflection condition can appropriately selected, the prisms are not limited in terms of angle and configuration. For example, a 60-degree dispersing prism and the like may be used. Examples of the commercially-available products of such prism include the same prism as the commercially-available product of the above-mentioned "transparent support made of glass".

Examples of the "optical filter" include a neutral density [ND] filter, a diaphragm lens, and the like. The neutral density [ND] filter (or, darker filter) is used for the purpose of adjusting an amount of incident laser light. Particularly, at the time of use of a detector with a narrow dynamic range, it is desirable to use the neutral density filter in order to conduct measurement with high precision.

The "polarization filter" is used for the purpose of making laser light to P polarized light which generates surface plasmon efficiently.

The "cut filter" is a filter to eliminate optical noises, such as outside light (illumination light at the outside of an apparatus), excitation light (transmitting components of excitation light), stray light (scattering components of the excitation light on respective places), scattering light of plasmon (scattering light which originates from excitation light the origin and is caused by the influence of the structure, extraneous matter, and the like on the surface of a sensor chip); and autofluorescence of fluorescent dyes. Examples of the cut filter include an interference filter, a color filter, and the like.

A "collective lens" is used for the purpose of collecting a fluorescent signal efficiently to the detector which measures an amount of fluorescence, and may be an arbitrary collective lens. As a simple collective lens, a commercially-available objective lens (for example, manufactured by NIKON or Olympus) which is used in a microscope and the like may be diverted. The magnification of the objective lens is preferably ten to 100 times.

Preferable examples of the "detector" include a photomultiplier tube (photomultiplier manufactured by Hamamatsu Photonics Co., Ltd.) from the viewpoint of super-high sensibility. Further, although sensitivity is low as compared with the photomultiplier tube, a CCD image sensor is also suitable, because the fluorescent signal can be observed as an image, noise light can be eliminate easily, and multi point measurement can be conducted.

[Process (d)]

The process (d) is a process of calculating the amount of analytes contained in an analyte liquid from the measurement results obtained by the above-mentioned process (c).

More concretely, the process (d) is a process of preparing a calibration curve by achieving measurement of target antigens or target antibodies with a known concentration and calculating the amount of analytes (target antigens) contained in a measured specimen from measurement signals based on the prepared calibration curve.

[Calculation of a S/N Ratio]

Further, in the process (d), the S/N ratio represented by the following formula (1a) can be calculated by use of "blank light emission signals" measured before the above process (b), "assay light emission signals" obtained by the above process (d), and "initial noise signals" measured in such a way that a metal base plate which is not modified is secured to a flow passage and the measurement is conducted while making ultrapure water to flow.

$$S/N = |Ia/Io|/In \quad (1a)$$

(In the formula (1a), Ia represents assay light emission signals, Io represents blank light emission signals, and In represents initial noise signals.)

In this connection, at the time of calculation of S/N, practically, the S/N ratio may calculated in the following formula (1b) in which "assay noise signals" in the case where the concentration of analytes included in an analyte liquid is 0 is made reference.

$$S/N = |Ia|/Ian \quad (1b)$$

(In the formula (1b), Ian represents assay noise signals and Ia represents assay light emission signals as same as that in the case of the above formula (1a).

[Kit]

It is desirable that a kit for an assay according to the present invention include everything needed at the time of operation of an assay method of the present invention except an analyte liquid. That is, the kit of the present invention includes at least a sensor chip (including at least a metal member, a SAM, a hydrophilic high molecule layer, and ligands on a support), and a moisturizer. Although a range of an average dried film thickness of a hydrophilic high molecule layer contained in the sensor chip is not limited specifically, the range is preferably 1 nm or more and 50 nm or less. The average dried film thickness can be measured by a commercially-available optical interferometry film thickness measuring device. Further, at the time of measurement, in the case where ligands and the like are immobilized in or on a hydrophilic high molecule layer, the measurement is conducted after removing the ligands and the like.

By use of the kit for an assays, blood or blood serum being analytes as an analyte liquid, and antibodies for a specific tumor marker, the content of the specific tumor marker can be detected with high sensibility and high accuracy. From this result, existence of the non-invasive cancer (pre-invasive cancer) before a clinical period which is undetectable by palpation etc can also be predicted with high accuracy.

Furthermore, a kit component may include a set of required equipment, such as reference materials for preparing calibration curve, explanatory leaflets, a microtiter plate capable of processing simultaneously many analytes.

EXAMPLE

Next, although the present invention will be explained still more in detail by showing examples, the present invention is not limited by these examples.

(Preparation of a Marker Second Antibody Liquid)

As the second ligands, used were antibodies in which anti-α fetoprotein [AFP] monoclonal antibodies (1D5; 2.5 mg/ml, manufacture by Japan Clinical Laboratories Inc.) were biotinylated by use of commercially-available biotinylation kit (manufactured by Dojin Chemical Laboratory Co., Ltd. The procedure of biotinylation was followed the protocol attached to the kit.

Next, the resulting biotinylated anti-AFP monoclonal antibody liquid and strept avidin marker Alexa Fluor(Registered Trademark) 647 (manufactured by Molecular Probes Corporation) liquid were mixed, and made to react by being stirred and mixed at a temperature of 4° C. for 60 minutes.

Finally, unreacted antibodies and unreacted enzymes were refined by use of a molecular-weight cut filter (manufactured by Nihon Millipore Co., Ltd.), where the Alexa Fluor (Registered Trademark) 647 marker anti-AFP monoclonal antibody liquid was obtained. The obtained marker second antibody liquid was preserved at 4° C. after measurement of protein concentration.

Example 1

(PRODUCTION OF A SENSOR CHIP) (A)

A transparent support made of glass with a refractive index [$n_d$] of 1.72 and a thickness of 1 mm ("S-LAL 10" manufactured by Ohara Corporation) was subjected to plasma cleaning. On one surface of the support, a chrome thin film was formed by a sputtering method, and then on the surface of the chrome thin film, a metal film being as a metal member was formed by a sputtering method, so that the metal film was formed on the transparent support. The chrome thin film had a thickness of 1 to 3 nm, and the metal film had a thickness of 42 to 47 nm.

The support on which the metal film was foamed in the above way was immersed in 10 ml of the ethanol solution of 10-amino-1-deccan thiol prepared to 1 mM for 24 hours, whereby a SAM was formed in one side of the metal film. Thereafter, the support was taken out from the ethanol solution, cleaned with each of ethanol and isopropanol, and then dried by use of an air gun.

Subsequently, the support on which the SAM was formed was immersed for one hour in a MES buffered saline solution [MES] (pH: 7.4, ion strength: 10 mM) which contained 1 mg/ml of carboxy methyl dextran [CMD] with a molecular weight of 500,000, 0.5 mM of N-hydroxysuccinic acid imide [NHS], and 1 mM of water-soluble carbodiimide [WSC], so that the CMD was immobilized as a hydrophilic high molecule layer in the SAM. Further, the support was immersed in a NaOH aqueous solution with 1 mol/l liter for 30 minutes, whereby unreacted succinic acid ester was made to hydrolyze. The CMD layer has an average film thickness of 70 nm and a density of 5.0 ng/mm$^2$.

Subsequently, the support was immersed in MES containing 50 mM of NHS and 100 mM of WSC for one hour, thereafter, further immersed in an anti-AFP monoclonal antibody (1D5; 2.5 μg/m, manufactured by Japan Clinical Laboratories, Inc.) solution for 30 minutes, whereby the first antibodies were immobilized as the first ligands on the CMD.

Further, PBS containing 1% by weight of bovine serum albumin [BSA] and 1 M of amino ethanol was made to flow in circulation for 30 minutes, thereby conducting a nonspecific adsorption preventing process.

On the support in which the first ligands having been subjected to the nonspecific adsorption preventing process were immobilized, a sheet which was made of poly-dimethyl siloxane [PDMS] had a flow passage with a height of 0.5 mm and a hole with a proper shape and size was disposed, and further around the sheet made of PDMS, a spacer made of silicone rubber was arranged (this spacer made of silicone rubber was on the condition that the spacer is not brought in contact with a solution fed to the flow passage. On the sheet made of PDMS and the spacer made of silicone rubber, a PMMA base plate in which a hole for introducing a liquid to be fed and a hole for discharging a liquid to be fed were formed in advance was disposed such that these holes were positioned in the inside of a region surrounded by the sheet made of PDMS (at this time, the PMMA base plate was arranged such that the surface on which the antibodies were immobilized became the inside of the flow passage. These members were bonded with pressure from the outside of the flow passage, and then the PMMA base plate was secured to a flow passage sheet (namely, the PDMS sheet) by use of screws, and the flow path sheet was secured to the support by use of screws, whereby a sensor chip (A) was produced.

(Implementation of an Assay)

An assay was implemented in accordance with the following processes by use of the sensor chip (A) produced as mentioned above.

As the process (a), 0.1 ml of a PBS liquid (analyte liquid) which contained 0.1 ng/ml of AFP as target antigens and 2M of urea was circulated in the flow passage of the sensor chip (A) obtained as mentioned above for 25 minutes.

As the cleaning process (1), after the process (a), in the flow passage of the sensor chip (A), a Tris buffered saline solution [TBS] containing 0.05% by weight of Tween 20 was circulated for 10 minutes so that the flow passage was cleaned.

As the process (b), after the cleaning process (1), in the flow passage of the sensor chip (A), 0.1 ml of the Alexa Fluor(Registered Trademark) 647 marker second antibodies (PBS liquid prepared so as to become 2 μg/ml) prepared in the above were fed and circulated for 5 minutes.

As the cleaning process (2), after the process (b), in the flow passage of the sensor chip (A), the TBS containing 0.05% by weight of Tween 20 was circulated for 10 minutes so that the flow passage was cleaned.

As the process (c), laser light (640 nm, 40 μW) was irradiated via a prism (manufactured by Sigma KOKI Co., Ltd.) onto another surface, where the metal film was not formed, of the sensor chip (A) having passed via the process (c), an amount of light was measured by detecting an amount of fluorescence emitted from the excited fluorescent dyes, and the measured amount of light was made as "assay light emission signals".

On the other hand, in above-mentioned processes (a) to (c), the amount of fluorescence was measured in the same way as the above except that a PBS liquid which did not contained AFP (0.0 ng/ml) and 2M of urea was circulated in the above process (a), and the measured amount of light was made as "assay noise signals".

Example 2

An assay was implemented by use of the sensor chip (A) in Example 1 in the same way as those in Example 1 except that in place of the analyte liquid in the process (a) in Example 1, 0.1 ml of a PBS liquid (analyte liquid) which contained 0.1 ng/ml of AFP as target antigens was used, and before the process (a), a mixed liquid in which 2M of urea was mixed in a Tris buffered saline liquid [IBS] containing 0.05% by weight of a cleaning liquid Tween 20 was fed and circulated for 10 minutes so that the flow passage was cleaned.

Example 3

(Production of a Sensor Chip) (B)

A transparent support made of glass with a refractive index $[n_d]$ of 1.72 and a thickness of 1 mm ("S-LAL 10" manufactured by Ohara Corporation) was subjected to plasma cleaning. On one surface of the support, a chrome thin film was formed by a sputtering method, and then on the surface of the chrome thin film, a metal film being as a metal member was formed by a sputtering method, so that the metal film was formed on the transparent support. The chrome thin film had a thickness of 1 to 3 nm, and the metal film had a thickness of 42 to 47 nm.

The support on which the metal film was formed in the above way was immersed in 10 ml of the ethanol solution of 10-carboxy-1-deccan thiol prepared to 1 mM for 24 hours, whereby a SAM was formed in one side of the metal film. Thereafter, the support was taken out from the ethanol solution, cleaned with each of ethanol and isopropanol, and then dried by use of an air gun.

Subsequently, the support on which the SAM was formed was immersed for one hour in a MES buffered saline solution [MES] (pH: 7.4, ion strength: 10 mM) which contained 1 mg/ml of AMINE-PEG-Carboxyric Acid (General Formula: $NH2-(CH_2CH_2O)_n-(CH_2)_m-COOH$, herein m=1 to 20) with a molecular weight, at a PEG chain portion< of 5,000, 0.5 mM of N-hydroxysuccinic acid imide [NHS], and 1 mM of a water-soluble carbodiimide [WSC], so that the PEG was immobilized as a hydrophilic high molecule layer in the SAM. The PEG layer has an average film thickness of 30 nm and a density of 4.0 ng/mm$^2$.

Subsequently, in the same way as that in Example 1, antibodies (first ligands) were immobilized in the PEG layer, and a nonspecific adsorption preventing process was performed.

On the support in which the first ligands having been subjected to the nonspecific adsorption preventing process were immobilized, a sheet which was made of poly-dimethyl siloxane [PDMS] had a flow passage with a height of 0.5 mm and a hole with a proper shape and size was disposed, and further around the sheet made of PDMS, a spacer made of silicone rubber was arranged (this spacer made of silicone rubber was on the condition that the spacer is not brought in contact with a liquid fed to the flow passage. On the sheet made of PDMS and the spacer made of silicone rubber, a PMMA base plate in which a hole for introducing a liquid to be fed and a hole for discharging a liquid to be fed were formed in advance was disposed such that these holes were positioned in the inside of a region surrounded by the sheet made of PDMS (at this time, the PMMA base plate was arranged such that the surface on which the antibodies were immobilized became the inside of the flow passage. These members were bonded with pressure from the outside of the flow passage, and then the PMMA base plate was secured to a flow passage sheet (namely, the PDMS sheet) by use of screws, and the flow path sheet was secured to the support by use of screws, whereby a sensor chip (B) was produced.

(Implementation of an Assay)

An assay was implemented in the same way as that in Example 1 by use of the sensor chip (B) produced as mentioned above.

Example 4

(Production of a Sensor Chip) (C)

A sensor chip (C) was produced in the same way as that in Example 1 except that 1 mg/ml of polyacrylic acid with a molecular weight of 5000 was use in place of 1 mg/ml of carboxy methyl dextran [CMD] with a molecular weight of 500,000 in the production of the sensor chip (A) in Example 1. The polyacrylic acid layer has an average film thickness of 30 nm and a density of 2.0 ng/mm$^2$.
(Implementation of an Assay)

An assay was implemented in the same way as that in Example 1 by use of the sensor chip (C) produced as mentioned above except that 2M of ammonium lactate was used in place of 2M of urea.

Example 5

(Production of a Sensor Chip) (D)

A sensor chip (D) was produced in the same way as that in Example 1 except that 1 mg/ml of polymethacrylic acid with a molecular weight of 5000 was use in place of 1 mg/ml of carboxy methyl dextran [CMD] with a molecular weight of 500,000 in the production of the sensor chip (A) in Example 1. The polymethacrylic acid layer has an average film thickness of 30 nm and a density of 0.9 ng/mm$^2$.
(Implementation of an Assay)

An assay was implemented in the same way as that in Example 1 by use of the sensor chip (D) produced as mentioned above except that 2M of glycerin was used in place of 2M of urea.

Example 6

(Production of a Sensor Chip) (E)

A sensor chip (E) was produced in the same way as that in Example 1 except that the average film thickness of the CMD layer was changed from 70 nm to 100 nm, and the density was changed from 1.9 ng/mm$^2$ to 6.0 ng/mm$^2$.
(Implementation of an Assay)

An assay was implemented in the same way as that in Example 1 by use of the sensor chip (E) produced as mentioned above.

Example 7

(Production of a Sensor Chip) (F)

A sensor chip (F) was produced in the same way as that in Example 1 except that the average film thickness of the CMD layer was changed from 70 nm to 10 nm, and the density was changed from 1.9 ng/mm$^2$ to 0.4 ng/mm$^2$.
(Implementation of an Assay)

An assay was implemented in the same way as that in Example 1 by use of the sensor chip (F) produced as mentioned above.

Comparative example 1

(Production of a Sensor Chip) (G)

A transparent support made of glass with a refractive index [n$_d$] of 1.72 and a thickness of 1 mm ("S-LAL 10" manufactured by Ohara Corporation) was subjected to plasma cleaning. On one surface of the support, a chrome thin film was formed by a sputtering method, and then on the surface of the chrome thin film, a metal film being as a metal member was formed by a sputtering method, so that the metal film was formed on the transparent support. The chrome thin film had a thickness of 1 to 3 nm, and the metal film had a thickness of 42 to 47 nm.

The support on which the metal film was formed in the above way was immersed in 10 ml of the ethanol solution of 10-carboxy-1-deccan thiol prepared to 1 mM for 24 hours, whereby a SAM was formed in one side of the metal film. Thereafter, the support was taken out from the ethanol solution, cleaned with each of ethanol and isopropanol, and then dried by use of an air gun.

Subsequently, the support was immersed for one hour in MES containing 50 mM (mole) of NHS and 100 mM of WSC, and then further immersed in an anti-AFP monoclonal antibody (1D5; 2.5 µg/m, manufactured by Japan Clinical Laboratories, Inc.) for 30 minutes, whereby the first antibodies (first ligands) were immobilized on the CMD.

Further, PBS containing 1% by weight of bovine serum albumin [BSA] and 1 M of amino ethanol was made to flow in circulation for 30 minutes, thereby conducting a nonspecific adsorption preventing process.

On the support in which the first ligands having been subjected to the nonspecific adsorption preventing process were immobilized, a sheet which was made of poly-dimethyl siloxane [PDMS] had a flow passage with a height of 0.5 mm and a hole with a proper shape and size was disposed, and further around the sheet made of PDMS, a spacer made of silicone rubber was arranged (this spacer made of silicone rubber was on the condition that the spacer is not brought in contact with a liquid fed to the flow passage. On the sheet made of PDMS and the spacer made of silicone rubber, a PMMA base plate in which a hole for introducing a liquid to be fed and a hole for discharging a liquid to be fed were formed in advance was disposed such that these holes were positioned in the inside of a region surrounded by the sheet made of PDMS (at this time, the PMMA base plate was arranged such that the surface on which the antibodies were immobilized became the inside of the flow passage. These members were bonded with pressure from the outside of the flow passage, and then the PMMA base plate was secured to a flow passage sheet (namely, the PDMS sheet) by use of screws, and the flow path sheet was secured to the support by use of screws, whereby a sensor chip (G) was produced.
(Implementation of an Assay)

An assay was implemented in the same way as that in Example 1 by use of the sensor chip (G) produced as mentioned above except that 0.1 ml of PBS liquid (analyte liquid) which contained 0.1 ng/ml of AFP as a target antigen was used in the process (a).

Comparative example 2

An assay was implemented in the same way as that in Example 1 by use of the sensor chip (A) produced in Example 1 except that 0.1 ml of PBS liquid (analyte liquid) which contained 0.1 ng/ml of AFP as a target antigen was used in the process (a) in Example 1.

Comparative example 3

An assay was implemented in the same way as that in Example 1 by use of the sensor chip (G) produced in Comparative example 1 except that 0.1 ml of PBS liquid which contained 0.1 ng/ml of AFP as a target antigen, 4% of polyethylene glycols [PEG] with a molecular weight of 5,000 and 2M of urea was used.

Comparative example 4

An assay was implemented in the same way as that in Example 1 by use of the sensor chip (G) produced in Comparative example 1 except that carboxy methyl dextran [CMD] with a molecular weight of 500,000 was added into 0.1 ml of PBS liquid containing 0.1 ng/ml of AFP as a target antigen and 2M of urea in such a way that the amount of CMD was adjusted (about 8%) to be equivalent to the amount of CMD (correspond to the amount of CMD contained in a film thickness of 100 nm and a density of 2 ng/mm²) used in the sensor chip (E) in Example 6, and the resulting liquid was used.

Comparative example 5

An assay was implemented in the same way as that in Example 1 by use of the sensor chip (G) produced in Comparative example 1 except that carboxy methyl dextran [CMD] with a molecular weight of 500,000 was added into 0.1 ml of PBS liquid containing 0.1 ng/ml of AFP as a target antigen and 2M of urea in such a way that the amount of CMD was adjusted (about 0.1%) to be equivalent to the amount of CMD (correspond to the amount of CMD contained in a film thickness of 10 nm and a density of 0.4 ng/mm²) used in the sensor chip (F) in Example 7, and the resulting liquid was used.

[Evaluation of S/N Ratio]

In the assay implemented in Examples 1 to 5 and Comparative examples 1 to 3, S/N was calculated with assay fluorescence signal and assay noise signal by the following formula, and the resulting S/N was evaluated based on the S/N in Comparative example 1 made as reference. The results are shown in Table 2.

$$S/N = (\text{assay light emission signal})/(\text{assay noise signal})$$

5: In the case where the value exceeds 10 times as compared with the S/N in Comparative example 1.

4: In the case where the value is 7 times or more and less than 10 times as compared with the S/N in Comparative example 1.

3: In the case where the value is 4 times or more and less than 7 times as compared with the S/N in Comparative example 1.

2: In the ease where the value is 2 times or more and less than 4 times as compared with the S/N in Comparative example 1.

1: In the case where the value is 1 times or more and less than 2 times as compared with the S/N in Comparative example 1.

As clear from Table 2, S/N of each of Examples 1 to 7 is remarkably improved to be 4 times or more as compared with S/N in Comparative example 1. In Comparative example 3, although hydrophilic high molecules and the moisturizer were used, the hydrophilic high molecules were not formed as a layer. Accordingly, since the immobilization of the first ligands was not performed efficiently, its S/N ratio was not improved so much as compared with Examples of the present invention. Moreover, in Comparative example 4, since the concentration of the hydrophilic high molecules in the liquid to be added was too high, the viscosity of the liquid became too high. As a result, the improvement of reactivity (S (assay light emission signal)) was lowered, so that the S/N ratio became extremely low.

What is claimed is:

1. An assay method with use of a sensor chip which includes a flow passage having a metal member on a support, a self-assembled monolayer (SAM) on another surface of the metal member which is not in contact with the support, a hydrophilic high molecule layer on the SAM, and first ligands immobilized at least one of in the hydrophilic high molecule layer and on the surface of the hydrophilic high molecular layer, and which is configured to be used for a fluorescence measuring apparatus with utilization of a surface plasmon-field enhanced Fluorescence Spectrometry, the assay method comprising the steps of:

(a) bringing an analyte liquid in contact with the first ligands of the sensor chip;

(b) making the sensor chip acquired through the process (a) to react with a conjugate material of fluorescent dyes and second ligands which may be the same with or different from first ligands contained in this sensor chip;

(c) irradiating laser light via a prism to another surface, on which the above metal member is not formed, of the support of the sensor chip acquired through the process (b) and measuring an amount of fluorescence emitted from the fluorescent dye excited with the irradiated laser light;

(d) calculating an amount of analyte contained in the analyte liquid from the measurement results obtained by the process (c);

TABLE 2

| | | Type of sensor chip | Hydrophilic high molecule layer | | | Addition of hydrophilic high molecules in an analyte liquid | Moisturizer | | S/N ratio |
| | | | Hydrophilic high molecule | Film thickness (nm) | Density (ng/mm²) | | In analyte liquid | In cleaning liquid | |
|---|---|---|---|---|---|---|---|---|---|
| Example | 1 | (A) | CMD | 70 | 5.0 | — | Urea | — | 5 |
| | 2 | | | | | | — | Urea | 5 |
| | 3 | (B) | PEG | 30 | 4.0 | | Urea | — | 3 |
| | 4 | (C) | Polyacrylic acid | 30 | 2.0 | | Ammonium lactate | — | 3 |
| | 5 | (D) | Polymethacrylic acid | 30 | 0.9 | | Glycerin | — | 3 |
| | 6 | (E) | CMD | 100 | 6.0 | | Urea | — | 5 |
| | 7 | (F) | CMD | 10 | 0.4 | | Urea | — | 3 |
| Comparative example | 1 | (G) | | — | | — | — | | Standard |
| | 2 | (A) | CMD | 70 | 5.0 | | | | 1 |
| | 3 | (G) | | — | | PEG | Urea | — | 2 |
| | 4 | | | | | CMD (about 8%) | Urea | — | 1 |
| | 5 | | | | | CMD (about 0.1%) | Urea | — | 2 | wherein the assay method further comprises the step of feeding and circulating a moisturizer to the flow passage to coexist with the hydrophilic high molecule layer at the time of start of the step (b), and wherein the moisturizer is at least one kind of material selected from the group consisting of urea, ethylene glycol, glycerin, ammonium lactate, pyrrolidone carboxylate, diol, lactic acid, hyaluronic acid, and chondroitin sulfate.

2. The assay method described in claim 1, wherein the hydrophilic high molecule layer contains high molecules in an amount of 0.001 ng/mm$^2$ or more and 30 ng/mm$^2$ or less.

3. The assay method described in claim 1, wherein the hydrophilic high molecule layer contains high molecules in an amount of 0.2 ng/mm$^2$ or more and 6 ng/mm$^2$ or less.

4. The assay method described in claim 1, wherein the hydrophilic high molecule layer contains at least one kind of high molecules selected from a group consisting of polysaccharide, polyethylene glycol, polyacrylic acid, and polymethacrylic acid.

5. The assay method described in claim 4, wherein the polysaccharide is dextran or dextran derivative.

6. The assay method described in claim 5, wherein the polysaccharide is carboxy methyl dextran.

7. The assay method described in claim 1, wherein the moisturizer is at least one kind of material selected from a group consisting of urea, ethylene glycol, glycerin, and ammonium lactate.

8. The assay method described in claim 1, wherein the hydrophilic high molecule layer has an average layer thickness of 3 nm or more and 130 nm or less.

9. The assay method described in claim 1, wherein the hydrophilic high molecule layer has an average layer thickness of 50 nm or more and 100 nm or less.

10. The assay method described in claim 1, wherein the moisturizer has a rehydration sample moisture content of 40 to 200% by Riviere method.

11. The assay method described in claim 1, wherein the first ligands are immobilized in the hydrophilic high molecule layer, and the immobilized first ligands are 10 femto-mol/cm$^2$ or more and 100 pico-mol/cm$^2$ or less.

12. The assay method described in claim 1, wherein the moisturizer is added preliminarily into a liquid containing analytes, and the liquid containing the analytes and the moisturizer are fed and circulated to the flow passage so that the moisturizer coexists with the hydrophilic high molecule layer.

13. The assay method described in claim 12, wherein the moisturizer has a concentration of 5 to 30% in the liquid containing the analytes and the moisturizer.

14. The assay method described in claim 1, wherein the moisturizer is added preliminarily into a cleaning liquid to clean an inside of the sensor chip before a liquid containing analyte is brought in contact with the ligands, and the cleaning liquid containing the moisturizer are fed and circulated to the flow passage with the hydrophilic high molecule layer so that the moisturizer coexists with the hydrophilic high molecule layer.

15. The assay method described in claim 14, wherein the moisturizer has a concentration of 5 to 30% in the cleaning liquid containing the moisturizer.

16. The assay method described in claim 1, wherein the support is a transparent support.

17. A kit for an assay for use in the assay method described in claim 1, comprising:

a sensor chip which includes a flow passage having a metal member on a support, a self-assembled monolayer (SAM) on another surface of the metal member which is not in contact with the support, a hydrophilic high molecule layer on the SAM, and first ligands immobilized at least one of in the hydrophilic high molecule layer and on the surface of the hydrophilic high molecule layer, and which is configured to be used for a fluorescence measuring apparatus; and a moisturizer, wherein the moisturizer is at least one kind of material selected from the group consisting of urea, ethylene glycol, glycerin, ammonium lactate, pyrrolidone carboxylate, diol, lactic acid, hyaluronic acid, and chondroitin sulfate.

18. The kit for an assay, described in claim 17, wherein the hydrophilic high molecule layer has a dried film thickness of 1 nm or more and 50 nm or less.

* * * * *